United States Patent [19]
Herrig

[11] Patent Number: 5,478,479
[45] Date of Patent: Dec. 26, 1995

[54] TWO-STAGE CELL WASH PROCESS CONTROLLED BY OPTICAL SENSOR

[75] Inventor: Russell Herrig, Sharon, Mass.

[73] Assignee: Haemonetics Corporation, Braintree, Mass.

[21] Appl. No.: 246,787

[22] Filed: May 20, 1994

[51] Int. Cl.[6] .................................................. B01D 17/038
[52] U.S. Cl. .................... 210/745; 210/94; 210/96.1; 210/787; 422/82.09; 436/45; 436/164; 494/1; 494/37; 604/5; 604/6
[58] Field of Search ............................. 210/85, 94, 143, 210/512.1, 745, 787, 789, 645, 360.1, 782, 96.1, 198.1, 368; 494/1, 37, 7, 84, 6; 604/4, 5, 6; 422/72, 82.05, 82.09; 436/45, 164, 177

[56] References Cited

U.S. PATENT DOCUMENTS

| | | | |
|---|---|---|---|
| 4,151,844 | 5/1979 | Cullis et al. | 210/789 |
| 4,482,342 | 11/1984 | Lueptow et al. | 494/21 |
| 4,668,214 | 5/1987 | Reeder | 494/37 |
| 4,806,252 | 2/1989 | Brown et al. | 210/745 |
| 4,828,716 | 5/1989 | McEwen et al. | 210/789 |
| 4,834,890 | 5/1989 | Brown et al. | 210/789 |
| 4,943,273 | 7/1990 | Pages | 494/41 |
| 5,076,911 | 12/1991 | Brown et al. | 210/745 |
| 5,308,506 | 5/1994 | McEwen et al. | 210/789 |
| 5,344,570 | 9/1994 | McLachlan et al. | 210/787 |
| 5,385,539 | 1/1995 | Maynard | 604/4 |

FOREIGN PATENT DOCUMENTS

| | | | |
|---|---|---|---|
| 2250699 | 6/1992 | United Kingdom | 604/6 |
| WO8901792 | 3/1989 | WIPO. | |

Primary Examiner—Joseph W. Drodge
Attorney, Agent, or Firm—Cesari and McKenna

[57] ABSTRACT

A method of washing salvaged blood includes separating higher density blood components from lower density blood components within a rotating centrifuge bowl. The separated blood components are washed with wash solution to remove free hemoglobin (Hgb), anticoagulant, cellular debris and other undesirable elements from the blood components. The previously separated blood components are re-suspended by braking the rotation of the centrifuge bowl to release the free Hgb, and other undesirable elements trapped in the red blood cell layer. The higher density blood components are then re-separated from the lower density blood components within the centrifuge bowl. The re-separated blood components are again washed with wash solution to further remove free Hgb and other undesirable elements from the blood components.

42 Claims, 3 Drawing Sheets

TWO-STAGE CELL WASH PROCESS CONTROLLED BY OPTICAL SENSOR

BACKGROUND OF THE INVENTION

Due to the risk of blood transmitted diseases and various transfusion reactions, it is common practice to collect blood lost by patients from Wounds during surgery for reinfusion back into the patient instead of infusing donated blood. The collected or salvaged blood typically contains high levels of free hemoglobin (Hgb) and cellular debris such as broken cell membranes. High levels of free Hgb are toxic and can cause kidney disease. Therefore, the removal of free Hgb is desirable. Broken cell membranes and other cellular debris must be removed before reinfusion because they may cause blood clotting and/or kidney necrosis. Other undesirable elements in salvaged blood include activated clotting proteins, anticoagulant, activated platelets and coagulation by-products. The effects are cumulative, such that as more blood is salvaged, washed and reinfused, the more undesirable elements are returned to the patient.

The free Hgb, cellular debris, anticoagulant and other undesirable elements are typically removed from salvaged blood by separating the blood into different fractions according to their densities in a rotating centrifuge bowl and washing out the free Hgb, anticoagulant, cellular debris and other undesirable elements with a continuous flow of saline solution. Although it is difficult to detect the presence or absence of cellular debris, anticoagulant and other undesirable elements, it is easy to detect the presence or absence of free Hgb due to its reddish color. Free Hgb levels are relatively easy to measure experimentally and free Hgb washout is proven to correlate well with washout of other undesirable elements. Therefore, it is common practice to concentrate on free Hgb washout in salvaged blood since the other undesirable elements will also be washed out.

SUMMARY OF THE INVENTION

Frequently, a continuous flow of saline solution does not remove all the free Hgb, cellular debris, anticoagulant and other undesirable elements from salvaged blood. The higher the initial concentration of free Hgb is in the salvaged blood, the higher the final concentration of free Hgb will be in the washed blood product. It is believed that some free Hgb, cellular debris, anticoagulant and other undesirable elements become trapped within the red blood cell layer when the rotating centrifuge bowl is filled with the salvaged blood. The trapped free Hgb, cellular debris, anticoagulant and other undesirable elements are difficult to remove during a continuous wash process and washing with increased volumes of saline solution provides diminishing returns in the amount of additional washout.

Accordingly, there is a need for a method of washing higher levels of free Hgb, cellular debris, anticoagulant and other undesirable elements from salvaged blood than obtainable with current methods.

The present invention provides a method of salvaging blood from a mixture of whole blood mixed with undesirable elements. The whole blood contains various blood components of varying densities. The mixture is separated into different fractions in accordance with the density of the components and undesirable elements within a rotating centrifuge bowl. The centrifuge bowl operates at a speed suitable for such separation. The separated blood components and undesirable elements are then washed with a wash solution to free undesirable elements from the separated blood components. After washing, the previously separated blood components and remaining undesirable elements are suspended by decelerating the rotation of the centrifuge bowl which forms a mixture of blood components and remaining undesirable elements. Subsequently, the mixture is again re-separated by accelerating the centrifuge bowl to its original operating speed and maintaining that speed. The re-separated blood components and undesirable elements are then washed again with wash solution to free additional undesirable elements from the separated components.

The undesirable elements mostly include free Hgb, cellular debris and anticoagulant. The undesirable elements are removed from the centrifuge bowl during washing by being displaced from the centrifuge bowl by incoming wash solution. Suspending the previously separated blood components and remaining undesirable elements releases undesirable elements trapped in the region occupied by higher density blood components and redistributes the remaining undesirable elements more evenly throughout the blood components within the bowl. As a result, after the blood components are re-separated, further undesirable elements can be washed out with wash solution because less undesirable elements remain trapped in the region occupied by the higher density blood components. This removes greater levels of undesirable elements from the salvaged blood than previously obtainable with current methods.

An effluent sensor monitors the presence or absence of blood components or undesirable elements such as red blood cells and free Hgb within fluid displaced from the centrifuge bowl when the centrifuge bowl is filled with blood or washed with wash solution. The blood and wash solution is pumped into the centrifuge bowl with a pump. The pump is capable of operating at a variety of speeds. The pumping speed of the pump is controlled in response to the presence or absence of blood components or undesirable elements within the monitored effluent fluid. Additionally, the volume of wash solution to be employed for washing blood components as well as the decision to conduct two wash stages is determined by the presence or absence of undesirable elements within the monitored effluent fluid.

BRIEF DESCRIPTION OF THE DRAWINGS

The foregoing and other objects, features and advantages of the invention will be apparent from the following more particular description of preferred embodiments of the drawings in which like reference characters refer to the same parts throughout the different views. The drawings are not necessarily to scale, emphasis instead being placed upon illustrating the principles of the invention.

DETAILED DESCRIPTION OF THE PREFERRED EMBODIMENTS

Figure 1:
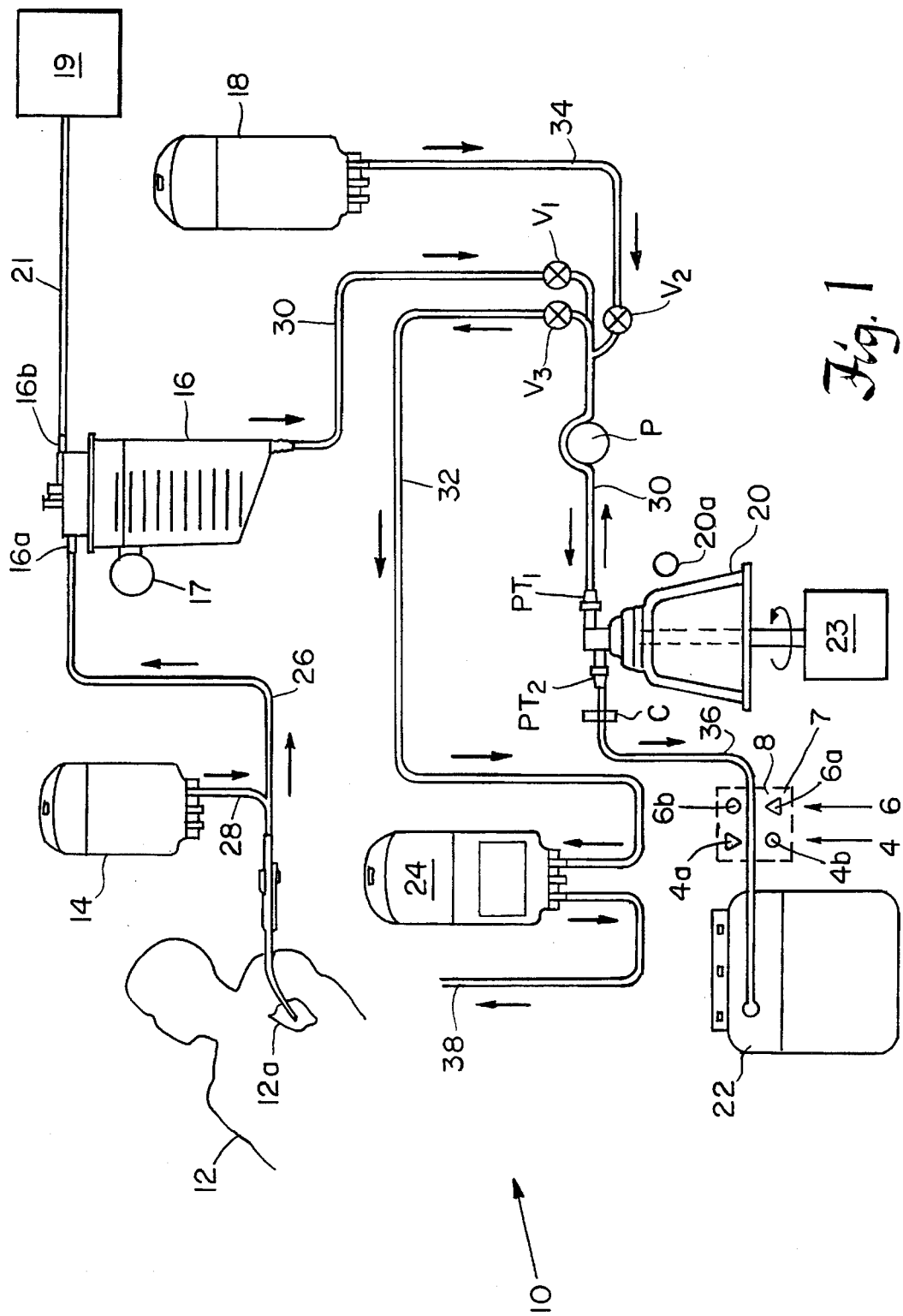
FIG. 1 is a schematic drawing of the present invention cell washing apparatus.

In FIG. 1, cell washing apparatus 10 includes a suction line 26 for suctioning blood lost from wound 12a of patient 12. Suction line 26 is in fluid communication with salvage reservoir 16 via port 16a. A bag 14, containing anticoagulant, is in fluid communication with suction line 26 via feed line 28. A vacuum source 19 is coupled to port 16b of reservoir 16 via vacuum line 21. Vacuum source 19 provides a vacuum within suction line 26 so that suction line 26 can suction blood from wound 12a into reservoir 16. A reservoir level sensor 17 senses the level of fluid within reservoir 16.

Figure 2:
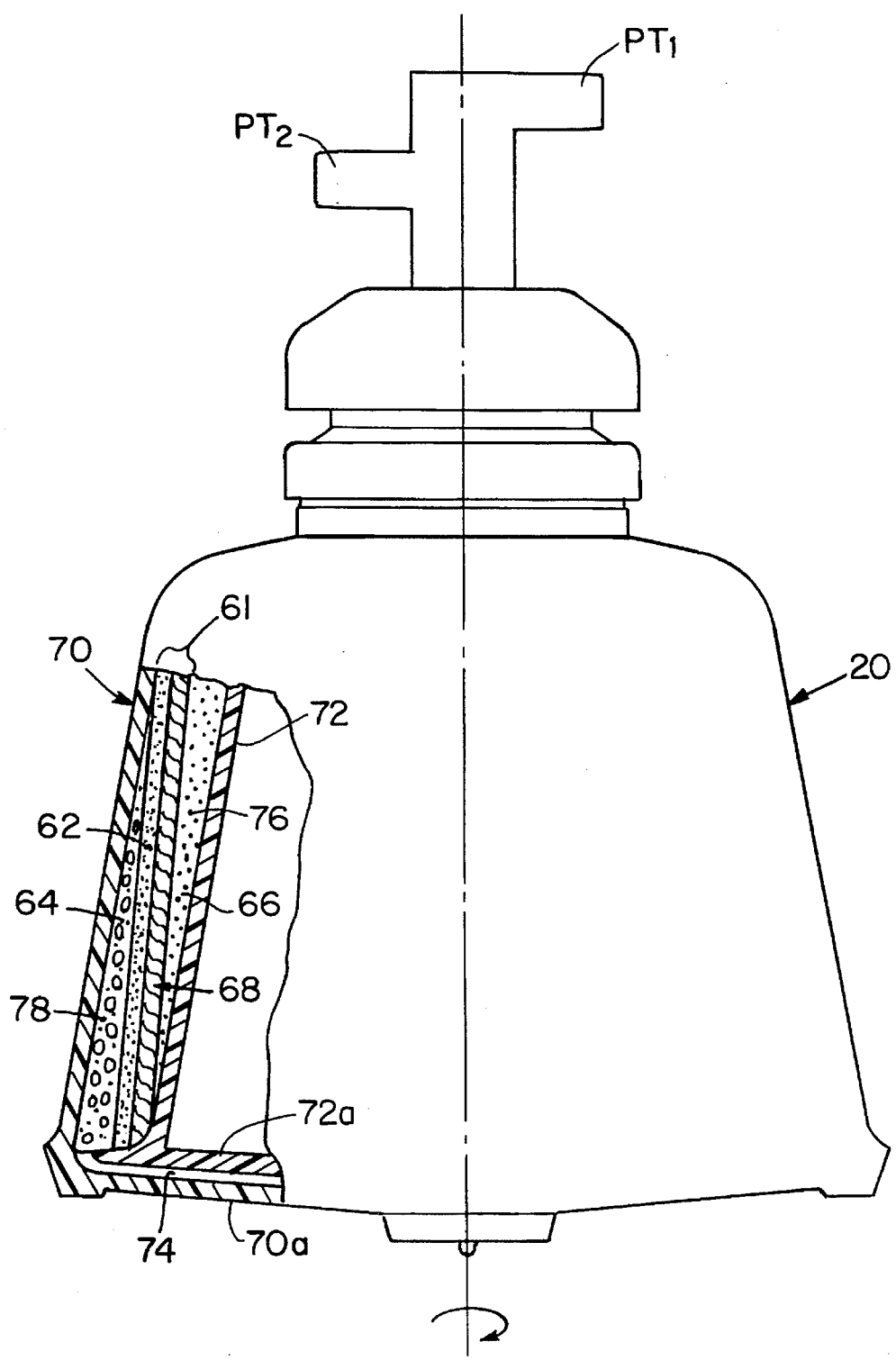
FIG. 2 is a side view of the centrifuge bowl with a portion broken away to illustrate the separated blood components.

Reservoir 16 is in fluid communication with centrifuge bowl 20 via line 30, valve $V_1$, and inlet port $PT_1$. Centrifuge 20 separates and washes salvaged blood received from reservoir 16. Centrifuge bowl 20 is rotated by motor 23. An optical sensor 20a senses the level of hematocrit within centrifuge bowl 20 by directing a beam of light into centrifuge bowl 20 which is reflected back to the sensor 20a by core 72 (FIG. 2). If the beam of light is not reflected back to sensor 20a, centrifuge bowl 20 is considered full of red blood cells (the bowl hematocrit is approximately 45%–55%). A waste container 22 for collecting waste washed from the salvaged blood is fluidly coupled to centrifuge bowl 20 via outlet port $PT_2$, and effluent line 36. Effluent line 36 passes through an optical line sensor 7 which senses the turbidity of fluid flowing through effluent line 36. Optical line sensor 7 controls the speed of pump P, the number of wash stages and the volume of wash solution employed for washing blood components. A bag 18, containing wash solution, is fluidly coupled to centrifuge bowl 20 via wash line 34, valve $V_2$, line 30, and inlet port $PT_1$. Centrifuge bowl 20 is in fluid communication with collection bag 24 via inlet port $PT_1$, line 30, valve $V_3$ and line 32. Line 38 allows fluid collected in collection bag 24 to be transferred into a secondary reinfusion bag (not shown) in which air is removed for pressurized reinfusion into patient 12 via a phlebotomy needle. Alternatively, line 38 allows fluid collected in collection bag 24 to be gravity fed into patient 12 via a phlebotomy needle. Valves $V_1$, $V_2$ and $V_3$ are remotely operated to control the directional flow of fluids pumped by pump P within apparatus 10. Pump P is a peristaltic pump for pumping fluids into and out of centrifuge bowl 20. Optionally, a clamp C can be included for clamping effluent line 36.

In operation, blood from wound 12a is suctioned from patient 12 via suction line 26. The suctioned blood is anticoagulated with anticoagulant dripping from bag 14 via feed line 28 and stored in reservoir 16. Reservoir level sensor 17 senses the level of salvaged blood within reservoir 16. Once a predetermined amount of salvaged blood is stored within reservoir 16, level sensor 17 activates pump P which begins what is to be referred to as the fill mode by pumping salvaged blood into centrifuge bowl 20 from reservoir 16 via line 30, valve $V_1$ and inlet port $PT_1$, with valve $V_1$ open and valves $V_2$ and $V_3$ closed. The rate of pump P is controlled by optical line sensor 7.

The blood enters the separation chamber 76 of centrifuge bowl 20 (FIG. 2) at the bottom of centrifuge bowl 20 via a feed tube (not shown) and radial passageway 74. Separation chamber 76 is defined by the outer wall 70 and the core 72 of centrifuge bowl 20. Radial passageway 74 is defined by the bottom 72a of core 72 and the bottom wall 70a of centrifuge bowl 20. As centrifuge bowl 20 is filled with blood, centrifuge bowl 20 is rotated by motor 23, separating the blood within separation chamber 76 into different fractions in accordance with the component densities. Centrifuge bowl 20 is preferably rotated at speeds ranging from about 4,800 to 5,650 revolutions per minute. Centrifugal forces separate the blood into higher density components, mainly red blood cells (RBCs) 64, intermediate density components, mainly white blood cells 62 and platelets 68, and lower density components, mainly plasma 66. The RBCs 64 are forced to the outer wall 70 of centrifuge bowl 20 while the plasma 66 remains nearer to the core 72 of centrifuge bowl 20. A "buffy coat" 61 is formed between the plasma 66 and the RBCs 64. The "buffy coat" 61 is made up of an inner layer of platelets 68 and an outer layer of white blood cells (WBCs) 62. Since free Hgb has a low density, most of the free Hgb remains within the plasma 66. The heavier undesirable elements such as cellular debris are primarily mixed with the "buffy coat" 61.

As separation chamber 76 is filled with blood, the RBC layer 64 moves in radially, resulting in its boundary rising upwards. Optical sensor 20a is positioned relative to centrifuge bowl 20 such that when separation chamber 76 is filled to approximately 50% hematocrit, the upwardly rising RBC layer scatters the beam of light generated by optical sensor 20a. As a result, optical sensor 20a does not receive a reflected beam of light from core 72 and optical sensor 20a determines that the centrifuge bowl 20 is full. Once optical sensor 20a determines that separation chamber 76 is filled to approximately 50% hematocrit, pump P stops pumping and the filling of centrifuge bowl 20 is terminated.

While the centrifuge bowl 20 is being filled with blood, the incoming blood displaces fluid (mostly plasma) from centrifuge bowl 20 into waste container 22 via outlet port $PT_2$ and effluent line 36. The displaced plasma also contains free Hgb. If optical line sensor 7 senses a high concentration of free Hgb in effluent line 36, a wash cycle (or mode) with two wash stages is required to reduce the concentration of free Hgb, cellular debris, anticoagulant and other undesirable elements to an acceptable level. If optical line sensor 7 senses a low concentration of free Hgb, a wash cycle (or mode) with only a single wash stage is necessary.

When only a single wash stage is required, a predetermined amount of wash solution for a single stage continuous wash is pumped from bag 18 into centrifuge bowl 20 by pump P via wash line 34, valve $V_2$, line 30 and inlet port PT1 with valves $V_1$ and $V_3$ closed and valve $V_2$ open. In the preferred embodiment, the wash solution is 0.9% saline solution, but alternatively, the saline concentration of the wash solution can be slightly varied. Additionally, the percent hematocrit to which separation chamber 76 is filled can also be varied. Valves $V_1$, $V_2$ and $V_3$ are preferably pneumatically operated and housed individually. However, valves $V_1$, $V_2$ and $V_3$ can be housed within a single manifold and can be activated by other suitable means such as with solenoids.

The wash solution enters separation chamber 76 via passageway 74 and flows through the separated blood components washing free Hgb, cellular debris, anticoagulant and other undesirable elements from the separated blood components. The free Hgb, cellular debris, anticoagulant and other undesirable elements washed from the separated blood components are displaced along with plasma and wash solution into waste container 22 by incoming wash solution via outlet port $PT_2$ and effluent line 36. If optical sensor 7 senses that the free Hgb level is still too high, the wash stage is extended for a brief period of time.

After the wash solution has been pumped into centrifuge bowl 20, pump P stops and valve $V_2$ closes, terminating the flow of wash solution into centrifuge bowl 20 to end the wash stage. The rotation of centrifuge bowl 20 is then terminated and pump P is reversed to pump the washed blood components remaining in centrifuge bowl 20 into collection bag 24 via line 30, valve $V_3$ and line 32 with valves $V_1$ and $V_2$ closed and valve $V_3$ open. The collected blood components can then be stored for later use or reinfused into patient 12 as discussed later.

In situations where a two-stage wash cycle is required, the first wash stage is performed in a manner similar to the single stage continuous wash cycle described above. The first stage of a two-stage wash cycle differs from the single-stage (continuous) wash cycle in that the first wash stage is not extended if the level of free Hgb is still high at the end of the first wash stage. After the flow of wash solution in the first wash stage is terminated, the rotation of centrifuge bowl 20 is then braked by reversing motor 23 to decelerate centrifuge bowl 20 which mixes or re-suspends the separated blood components remaining within bowl 20. This releases any free Hgb, cellular debris, anticoagulant and other undesirable elements 78 trapped within the RBC layer 64 and redistributes the free Hgb, cellular debris, anticoagulant and other undesirable elements more evenly with the remaining contents of separation chamber 76. In the preferred embodiment, centrifuge bowl 20 is braked preferably for a period of time ranging from about 2 to 5 seconds to a dead stop to cause mixing. Alternatively, other suitable braking time periods and speeds can be employed. For example, centrifuge bowl 20 can be braked to a speed of less than 100 revolutions per minute or can be decelerated simply by cutting power to motor 23.

Once the separated blood components are mixed together, the braking of centrifuge bowl 20 is terminated and the rotation of centrifuge bowl 20 is accelerated back to operating speed, re-separating the blood components into different fractions within separation chamber 76. A second predetermined amount of wash solution for the second wash stage is then pumped from bag 18 into centrifuge bowl 20 by pump P via wash line 34, valve $V_2$, line 30 and inlet port $PT_1$ with valves $V_1$ and $V_3$ closed and valve $V_2$ open. This washes free Hgb, cellular debris, anticoagulant and other undesirable elements from the separated blood components which were released from the RBC layer 64 when the blood components were re-suspended or mixed. The free Hgb, cellular debris, anticoagulant and other undesirable elements are displaced into waste container 22 by incoming wash solution. If, at this time, optical sensor 7 senses that the level of free Hgb is still too high, the second wash stage is extended for a brief period of time. An optional clamp "C" on effluent line 36 can be employed so that waste reservoir 22 can be disconnected from centrifuge bowl 20 without spilling the contents.

After the free Hgb, cellular debris, anticoagulant and other undesirable elements are displaced into waste container 22, centrifuge bowl 20 is braked to a stop. Pump P is reversed to pump the washed blood components remaining in centrifuge bowl 20 into collection bag 24 via line 30, valve $V_3$ and line 32 with valves $V_1$ and $V_2$ closed and valve $V_3$ open. The blood components collected in collection bag 24 can be stored for later use or can be reinfused into patient 12. If the blood components are reinfused into patient 12, the blood components are transferred from collection bag 24 to a secondary infusion bag (not shown) where air is removed so that the blood components can be reinfused into patient 12 under pressure. Alternatively, the blood components can be gravity fed from collection bag 24 into patient 12 so that air does not mix with the blood components.

The amount of wash solution used in the first wash stage in a two-stage wash cycle is preferably twice the amount of wash solution used in the second wash stage. For example, in the preferred embodiment, the first wash stage can be performed with 1000 milliliters of wash solution, while the second wash stage is performed with 500 milliliters of wash solution. Additionally, 250 milliliters of wash solution can be employed for extending the second wash stage. However, other suitable ratios and volumes of wash solution for the first wash stage, second wash stage or extended wash can be employed depending on the size of the centrifuge bowl used and the concentration of free Hgb, cellular debris, anticoagulant and other undesirable elements in the salvaged blood.

The rate at which blood and wash solution is pumped into centrifuge bowl 20 by pump P during fill mode is controlled by optical line sensor 7 on effluent line 36 which senses the quality of the salvaged blood entering centrifuge bowl 20 based on the turbidity of its effluent within effluent line 36. Likewise, the rate at which wash solution is pumped into centrifuge bowl during wash mode by pump P is controlled by optical line sensor 7 on effluent line 36, which senses the level of free Hgb and cellular debris in effluent within effluent line 36. If optical line sensor 7 detects red blood cells spilling into effluent line 36 from centrifuge bowl during the fill or wash modes, the speed of pump P is slowed from an initial intermediate speed.

Additionally, the number of wash stages and the volume of wash solution employed can be determined by optical line sensor 7. Cell washing apparatus 10 is preferably set up to be capable of performing either a single-stage cell wash cycle or a two-stage cell wash cycle depending upon the quality of the salvaged blood. When centrifuge bowl 20 is filled with blood, fluid displaced from centrifuge bowl 20 into effluent line 36 passes through optical line sensor 7 which detects the concentration of free Hgb of the fluid exiting the centrifuge bowl 20. The concentration of free Hgb in effluent line 36 provides a good representation of overall blood quality. If the level of free Hgb is low, a single-stage wash cycle with the normal volume of wash solution is sufficient to wash free Hgb from the separated blood components and a two-stage wash cycle is unnecessary. If the level of free Hgb is high, a two-stage wash cycle with an increased volume of wash solution is employed. For example, a normal volume of wash solution for a standard size centrifuge bowl is preferably 1000 milliliters while a normal volume for a low volume centrifuge bowl is 750 milliliters. The total increased volume of wash solution for a two-stage wash cycle is preferably 1500 milliliters for a standard size centrifuge bowl and 1000 milliliters for a low volume centrifuge bowl. Furthermore, if a wash cycle is extended, an additional 250 milliliters of wash solution is employed.

Line sensor 7 includes a housing 8 having a groove through which effluent line 36 passes. Two LED-detector units 4 and 6 straddling effluent line 36 are housed within housing 8. LED-detector unit 4 includes an LED 4a for emitting light and a detector 4b for detecting light emitted from LED 4a. LED-detector unit 6 includes an LED 6a for emitting light and a detector 6b for detecting light emitted by LED 6a. LED 4a emits light of a wavelength of 670 nanometers (red light) and LED 6a emits light of a wavelength of 565 nanometers (yellow-green light). LEDs 4a and 6a are located on the opposite side of effluent line 36 from detectors 4b and 6b. Light emitted by LEDs 4a and 6a passes through effluent line 36 and is detected by respective detectors 4b and 6b. LEDs 4a and 6a are located on opposing sides of effluent line 36 to reduce the possibility that detectors 4b and 6b will detect light emitted from the wrong LED.

The yellow-green light emitted by LED 6a is absorbed by free Hgb, and absorbed and scattered by RBCs. The red light emitted by LED 4a is absorbed and scattered by RBCs but is not readily absorbed by free Hgb. Due to the different wavelengths of light employed for LED-detector units 4 and 6, LED-detector unit 6 is sensitive to detecting small amounts of free Hgb while LED-detector unit 4 is relatively insensitive to free Hgb levels. Both LED-detector units 4 and 6 detect RBCs and cell stroma in effluent line 36. If both LEDs-detector units 4 and 6 indicate high levels of RBCs in effluent line 36, pump P is slowed down to avoid spilling RBCs from centrifuge bowl 20. Line sensor 7 can detect hematocrits as low as 1% within effluent line 36, which allows the system to reduce the pump speed rapidly and thus alleviate red blood cell spillage from centrifuge bowl 20. During fill mode, both LED-detector units are relied upon while the LED-detector unit 6 is helpful at the end of wash when free Hgb is usually at a low level. LED-detector unit 4 is monitored during the wash mode to make sure that RBCs are not spilled into effluent line 36.

Detectors 4b and 6b produce a voltage which is proportional to the light received from respective LEDs 4a and 6a. If there is free Hgb or RBCs present within effluent line 36, light emitted by the LEDs is scattered or absorbed, reducing the amount of light received by detectors 4b and 6b, thereby reducing their respective voltage outputs. As a result, the presence of free Hgb and RBCs within effluent line 36 can be detected by monitoring the voltage output of detectors 4b and 6b.

The voltage output from detectors 4b and 6b is converted by an analog/digital convertor into digital counts. As a result, the concentration of free Hgb or RBCs within effluent line 36 is correlated into digital counts. The digital counts are used to specify the pumping rates of pump P. The pump rates for various digital counts and bowl sizes are preprogrammed. Sample pump rates, digital counts and bowl sizes are depicted in Table 1. The values listed in Table 1 are merely examples since actual values vary depending upon the calibration of optical line sensor 7 and the type of analog/digital converter. In this manner, the pump rate of pump P is controlled (increased or decreased) upon the effluent quality in effluent line 36 sensed by optical sensor 7. In Table 1, there are five levels of bowl effluent quality as indicated by LED-detector unit 4. These levels are defined by digital count limits stored within the memory of a microprocessor coupled to the LED-detector units. The microprocessor reads the effluent quality from the line sensor 7 based upon the digital count output. The pump speed is determined by the preprogrammed pump speed rate for a given digital count range as depicted in Table 1. Exceeding the bounds of any range causes the limit to shift preferably by 35 counts to make it more difficult to shift back to the previous pump speed. This provides more stability to the control system by preventing frequent pump speed oscillations. Alternatively, the bounds of a range can be programmed to shift by more than 35 counts or less than 35 counts. Additionally, more than five levels or less than five levels of bowl effluent quality can be employed, if needed.

TABLE 1

| Digital Counts Range | FILL Pump Rates (ml/min) | |
|---|---|---|
| | Standard Bowl | Low-Vol. Bowl |
| x ≧ 1500 | 600 | 300 |
| 1100 ≦ x < 1500 | 500 | 275 |
| 750 ≦ x < 1100 | 400 | 250 |
| 500 ≦ x < | 350 | 225 |

TABLE 1-continued

| Digital Counts Range | FILL Pump Rates (ml/min) | |
|---|---|---|
| | Standard Bowl | Low-Vol. Bowl |
| 750 x < 500 | 300 | 20 |

Figure 3:
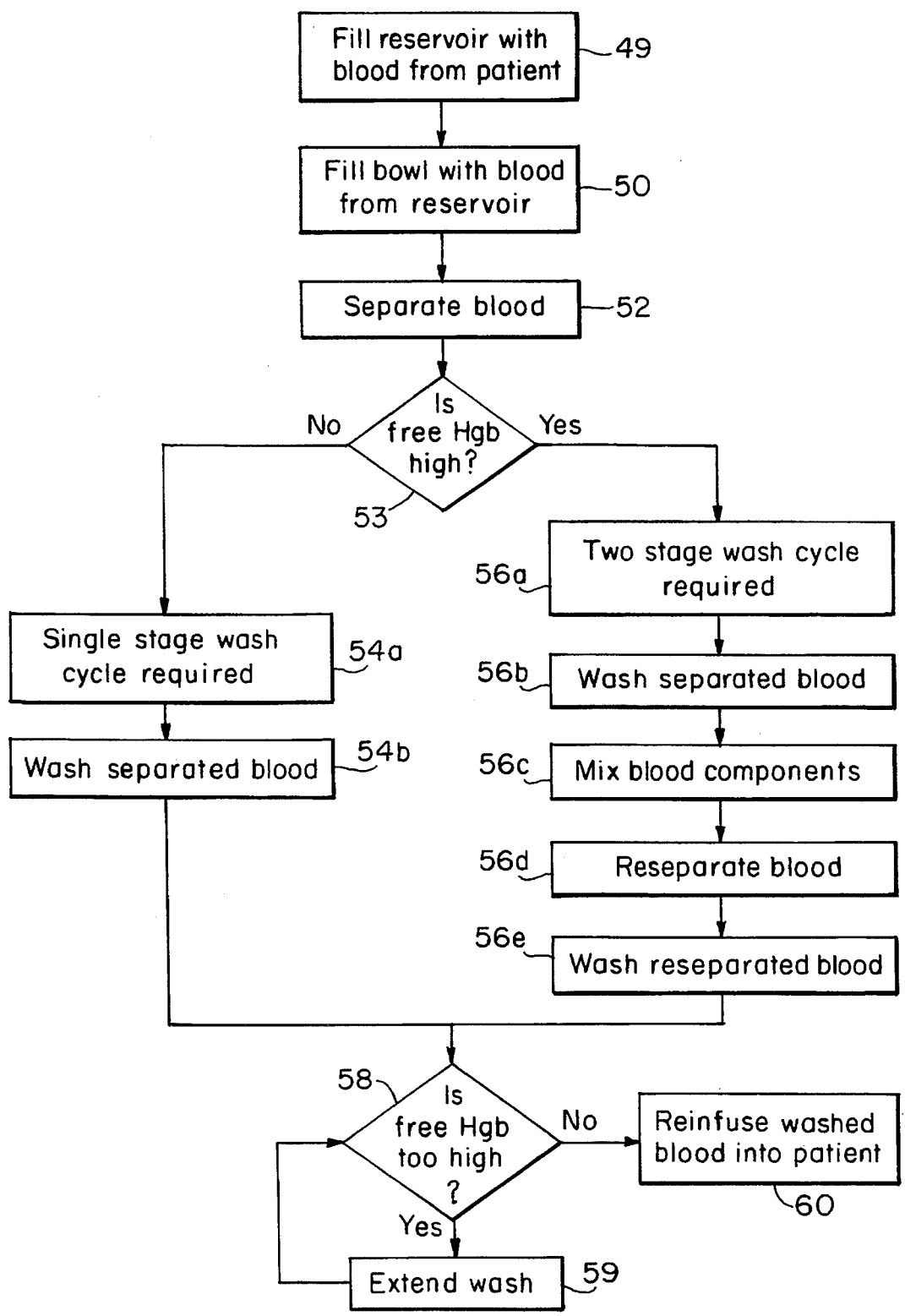
FIG. 3 is a flow chart of the software used in the present invention cell washing apparatus.

FIG. 3 depicts a flow chart for the preferred software for controlling cell washing apparatus 10. At step 49, a first filler fills reservoir 16 with blood from patient 12. At step 50, a second filler fills centrifuge bowl 20 with blood from reservoir 16. At step 52, a separator separates the blood in centrifuge bowl 20 as the blood fills centrifuge bowl 20. At step 53, if the level of free Hgb within effluent line 36 is low, only a single-stage wash cycle is required at step 54a and a first washer washes the separated blood in centrifuge bowl 20 with wash solution from bag 18 at step 54b. After the wash stage at step 54b, if the free Hgb is low at step 58, the washed blood is reinfused into patient 12 at step 60 by a reinfuser. If the free Hgb is high at step 58, an extender at step 59 extends the wash stage to reduce the level of free Hgb before reinfusion into the patient.

If the level of free Hgb is high during the fill and separate modes at step 53, a two-stage wash cycle is specified at step 56a. At step 56b, the first washer washes the separated blood in centrifuge bowl 20 with wash solution from bag 18. At step 56c, a mixer mixes or resuspends the washed blood components in centrifuge bowl 20. At step 56d, a re-separator re-separates the blood components within centrifuge bowl 20. At step 56e, a second washer washes the re-separated blood components within centrifuge bowl 20. At step 58, if the free Hgb is low, a reinfuser reinfuses the washed blood into patient 12 at step 60. At step 58, if the level of free Hgb is still high, the extender at step 59 extends the wash stage to reduce the level of free Hgb before reinfusion into the patient. Although the flow chart in FIG. 3 depicts the decision to employ either a single-stage wash cycle or a two-stage wash cycle during the fill and separate modes, alternatively, the decision can be made after a single wash stage has been performed.

Although cell washing apparatus 10 is preferably controlled by software, alternatively, cell washing apparatus 10 can be controlled by firmware or hardware. Additionally, other process steps can be added and the order of the steps involved can be varied.

Equivalents

While this invention has been particularly shown and described with references to preferred embodiments thereof, it will be understood by those skilled in the art that various changes in form and details may be made therein without departing from the spirit and scope of the invention as defined by the appended claims. Although FIG. 2 depicts a bowl similar to the Latham-type bowl disclosed in U.S. Pat. No. 4,300,717, other suitable bowls may be employed such as those disclosed in U.S. Pat. Nos. 4,943,273 and 4,983,158.

What is claimed is:

1. A method of processing blood mixed with undesirable elements not normally found in healthy whole blood, to remove the undesirable elements, the method comprising the steps of:

separating the blood into components according to relative densities of the components with a rotating centrifuge bowl;

providing a port through which fluid exits the bowl, said fluid having a concentration of undesirable elements;

monitoring said exiting fluid with an optical sensor having an output signal indicative of the concentration of undesirable elements;

comparing the concentration indicated by the output signal with a first predetermined concentration;

determining at least one of
  (a) a number of wash stages, in addition to a first wash stage, wherein a wash stage comprises admitting a wash-stage volume of wash solution into the rotating centrifuge bowl and thereafter recombining said components; and
  (b) at least one wash-stage volume of wash solution based on the comparison of the concentration indicated by the output signal with the first predetermined concentration; and following said determination, washing the blood in accordance therewith.

2. The method of claim 1 wherein a wash-stage volume of wash solution is admitted at a rate, the rate being determined by comparison of the concentration of undesirable elements in the exiting fluid indicated by the output signal with a second predetermined level.

3. The method of claim 1 wherein the undesirable elements comprise at least one of free Hgb, cellular debris, clotting proteins, activated platelets, coagulation byproducts and anticoagulant.

4. The method of claim 3 wherein the undesirable elements comprise free Hgb.

5. The method of claim 1 further comprising the step of admitting the blood to be separated into the centrifuge bowl.

6. The method of claim 5 wherein the admitted blood is present in an amount in the bowl and further comprising the step of monitoring the amount with an optical sensor and wherein the admitting of blood ceases when the amount reaches a predetermined value.

7. The method of claim 5 further comprising the step of filling a reservoir with blood collected from a wound on a patient and wherein the blood to be separated is admitted to the bowl from the reservoir.

8. The method of claim 7 further comprising the step of reinfusing at least one of the components into the patient.

9. The method of claim 1 wherein the step of washing the blood comprises admitting a first wash-stage volume of wash solution into the bowl, the admission of the first wash-stage volume causing a first amount of fluid to exit the bowl.

10. The method of claim 9 wherein the step of washing the blood further comprises the steps of:

recombining the components by decelerating the centrifuge bowl;

re-separating the blood into the components by re-accelerating the centrifuge bowl;

admitting a second wash-stage volume of wash solution into the centrifuge bowl, the admission of the second wash-stage volume causing a second amount of fluid to exit the bowl;

monitoring said second amount of fluid with the optical sensor having an output signal indicative of the concentration of undesirable elements in the exiting fluid; and admitting an additional volume of wash solution into the bowl if the concentration of undesirable elements indicated by the output signal is greater than a second predetermined concentration, the admission of the additional volume causing a third amount of fluid to exit the bowl.

11. The method of claim 10 wherein the separated components include higher density components in which resident undesirable elements remain suspended after admitting the first wash-stage volume of wash solution into the bowl, said resident undesirable elements being redistrubuted throughout the components as a result of the decelerating of the bowl.

12. The method of claim 10 in which the centrifuge bowl is decelerated by braking the centrifuge bowl.

13. The method of claim 12 in which in the braking of the centrifuge bowl it is braked to a stop.

14. The method of claim 9 wherein the step of washing the blood further comprises the steps of:

monitoring the first amount of fluid with the optical sensor having an output signal indicative of the concentration of undesirable elements in the further exiting fluid; and admitting a second volume of wash solution into the bowl if the concentration of undesirable elements indicated by the output signal is greater than a second predetermined concentration, the admission of the second volume causing a second amount of fluid to exit the bowl.

15. The method of claim 1 wherein at least one wash-stage volume of wash solution is determined based on the comparison of the concentration indicated by the output signal with the first predetermined concentration.

16. The method of claim 1 further comprising the steps of:

monitoring said exiting fluid with an optical sensor having an output signal indicative of a level of red blood cells in the exiting fluid; and admitting a volume of wash solution at a rate, the rate being determined by at least one of:
  (a) comparison of the concentration of undesirable elements in the exiting fluid indicated by the output signal indicative of the concentration of undesirable elements with a second predetermined concentration; and
  (b) comparison of the concentration of red blood cells in the exiting fluid indicated by the output signal indicative of the level of red blood cells with a predetermined level.

17. The method of claim 16 wherein the rate is determined by comparison of the concentration of red blood cells in the exiting fluid indicated by the output signal indicative of the level of red blood cells with a predetermined level.

18. The method of claim 1 wherein at least one wash-stage volume of wash solution passes through the blood.

19. The method of claim 1 further comprising the steps of:

monitoring said exiting fluid with an optical sensor having an output signal indicative of a level of red blood cells in the exiting fluid admitting the blood into the centrifuge bowl at a rate, the rate being determined by comparison of the level of red blood cells indicated by the output signal with a predetermined level.

20. The method of claim 1 wherein a number of wash stages is determined based on the comparison of the concentration indicated by the output signal with the first predetermined concentration.

21. The method of claim 1 wherein the step of monitoring the exiting fluid with an optical sensor comprises:

a) transmitting light from a plurality of light sources through the exiting fluid; and (b) detecting transmitted light with detectors to produce the output signal.

22. The method of claim 21 wherein each light source emits light of a different wavelength.

23. The method of claim 22 wherein a substance in the exiting fluid is more translucent to the light of a first one of said light sources than it is to the light of a second one of said light sources.

24. The method of claim 23 wherein a second substance in the exiting fluid is more translucent to the light of the second one of said light sources than it is to the light of the first one of said light sources.

25. An apparatus for removing undesirable elements, not normally found in healthy whole blood, from blood mixed with the undesirable elements, the apparatus comprising:

a rotatable centrifuge bowl for separating the blood into components according to relative densities of the components;

a controllable pump for admitting wash solution into the centrifuge bowl;

a port through which fluid exits the bowl:

an optical sensor for monitoring said fluid exiting the bowl and generating an output signal indicative of a concentration of said undesirable elements in the exiting fluid;

control means, operatively coupled to the pump, for comparing the concentration indicated by the output signal with a first predetermined concentration to determine, before actuating the pump to admit any wash solution into the bowl, at least one of:

(a) a number of wash stages, wherein a wash stage comprises admitting a wash-stage volume of wash solution into the rotating centrifuge bowl and thereafter recombining said components; and (b) at least one wash-stage volume of wash solution, the control means operable for operating the pump so as to wash the blood in accordance with said determination.

26. The apparatus of claim 25 further comprising a means for reinfusing at least one of the components into the patient.

27. The apparatus of claim 25 wherein the control means is operable for comparing concentration indicated by the output signal of the optical sensor with the first predetermined concentration to determined the at least one wash-stage volume of wash solution to be admitted into the bowl.

28. The apparatus of claim 25 wherein the control means operable compares the concentration indicated by the output signal of the optical sensor with the first predetermined concentration to determined the number of wash stages.

29. The apparatus of claim 25 further comprising means for admitting blood into the bowl.

30. The apparatus of claim 29 further comprising a means for filling a reservoir with blood collected from a wound on a patient and wherein the means for admitting blood into the bowl conveys the blood from the reservoir.

31. The apparatus of claim 29 wherein the admitted blood is present in an amount in the bowl and further comprising:

a) means for monitoring the amount of blood; and b) means for controlling the means for admitting blood such that the admitting ceases when the amount reaches a predetermined value.

32. The apparatus of claim 29 wherein the means for admitting blood into the bowl admits the blood at a rate and further comprising:

a sensor generating an output signal indicative of a level of red blood cells in the exiting fluid; and control means, operatively coupled to the pump, for comparing the level of red blood cells in the exiting fluid indicated by the output signal with a predetermined level, the control means regulating the rate.

33. The apparatus of claim 25 further comprising:

means for decelerating the centrifuge bowl to recombine the components; and means for reaccelerating the bowl to reseparate the blood into the components.

34. The apparatus of claim 25 wherein the pump admits the wash solution at a rate, and further comprising control means, operatively coupled to the pump, for comparing the concentration of undesirable elements indicated by the output signal with a second predetermined concentration, the control means regulating the rate.

35. The apparatus of claim 25 wherein the optical sensor comprises a plurality of light sources and light detectors, each light source emitting light which passes through the fluid exiting the bowl and each detector receiving said light after it passes through the fluid.

36. The apparatus of claim 35 wherein two of said light sources are located on opposite sites of the exiting fluid from one another.

37. The apparatus of claim 35 wherein each light source emits light of a different wavelength.

38. The apparatus of claim 37 wherein a first one of said light sources emits red light.

39. The apparatus of claim 38 wherein a second one of said light sources emits yellow-green light.

40. The apparatus of claim 37 wherein a first one of said light sources emits light that is absorbed more strongly by a substance in the exiting fluid than is the light emitted by a second one of said light sources.

41. The apparatus of claim 40 wherein the second one of said light sources emits light that is absorbed more strongly by a second substance in the exiting fluid than is the light emitted by the first one of said light sources.

42. The apparatus of claim 25 wherein the pump admits wash fluid into the bowl at a rate and further comprising:

a sensor generating an output signal indicative of a level of red blood cells in the exiting fluid; and control means, operatively coupled to the pump, for comparing the level of red blood cells in the exiting fluid indicated by the output signal with a predetermined level, the means controlling the rate.

* * * * *